United States Patent [19]

Walther et al.

[11] Patent Number: 5,575,751

[45] Date of Patent: Nov. 19, 1996

[54] DEVICE FOR MEASURING INCIDENT LIGHT IN A BODY CAVITY

[75] Inventors: McClellan M. Walther, Gaithersburg; Thomas F. DeLaney, Silver Spring; Frank Harrington, Catonsville; Paul D. Smith, Annapolis; Walter S. Friauf, Bethesda, all of Md.

[73] Assignee: The United States of America as represented by the Department of Health and Human Services, Washington, D.C.

[21] Appl. No.: 294,892

[22] Filed: Aug. 22, 1994

Related U.S. Application Data

[63] Continuation of Ser. No. 883,013, May 14, 1992, abandoned.

[51] Int. Cl.⁶ .................. A61B 1/00; A61B 1/06; A61B 5/05
[52] U.S. Cl. .......... 600/104; 600/135; 600/128; 600/182; 128/653.1; 128/665
[58] Field of Search .......... 128/6–9, 11, 653.1, 128/658, 665, 736; 606/11–16, 2; 607/88, 90, 93; 362/32, 5; 385/116, 117, 119, 137, 104, 111; 600/104, 182, 135, 128

[56] References Cited

U.S. PATENT DOCUMENTS

| | | |
|---|---|---|
| D. 254,270 | 2/1980 | Ziegler . |
| 1,650,959 | 11/1927 | Pitman ..................... 128/6 |
| 4,066,071 | 1/1978 | Nagel . |
| 4,266,549 | 5/1981 | Kimura ............... 128/395 X |
| 4,461,283 | 7/1984 | Doi ............... 606/15 |
| 4,628,207 | 12/1986 | Elfert et al. ............ 385/117 X |
| 4,648,892 | 3/1987 | Kittrell et al. ............ 606/12 X |
| 4,681,122 | 7/1987 | Winters et al. ............ 128/736 |
| 4,735,501 | 4/1988 | Ginsburgh et al. ........ 128/4 X |
| 4,756,303 | 7/1988 | Kawashima et al. ........ 128/6 |
| 4,784,132 | 11/1988 | Fox et al. ............ 606/15 |
| 4,848,323 | 7/1989 | Marijnissen ............ 128/6 |
| 4,979,497 | 12/1990 | Matsura et al. . |
| 4,986,622 | 1/1991 | Martinez . |
| 4,988,163 | 1/1991 | Cohen et al. . |
| 4,991,564 | 2/1991 | Takahashi et al. . |
| 5,016,614 | 5/1991 | MacAllister . |
| 5,041,109 | 8/1991 | Abela ............ 606/15 |
| 5,050,585 | 9/1991 | Takahashi . |
| 5,099,827 | 3/1992 | Melzer et al. ............ 128/4 |
| 5,108,364 | 4/1992 | Takezawa et al. ............ 128/736 X |
| 5,145,863 | 9/1992 | Dougherty et al. ............ 128/898 X |
| 5,161,531 | 11/1992 | Parsons et al. ............ 128/665 X |
| 5,188,596 | 2/1993 | Condon et al. ............ 128/6 X |
| 5,220,927 | 6/1993 | Astrahan et al. ............ 128/736 X |
| 5,359,685 | 10/1994 | Waynant et al. ............ 385/43 X |

FOREIGN PATENT DOCUMENTS 3245846  7/1983  Germany ............ 606/12

Primary Examiner—Richard J. Apley
Assistant Examiner—John P. Leubecker
Attorney, Agent, or Firm—Lowe, Price, LeBlanc & Becker

[57] ABSTRACT

A device for measuring incident light in a remote situs such as a body cavity which includes a central tubular member through which light is delivered to the remote situs and one or more auxiliary tubular members through which incident light in the remote situs is transmitted to a light detector. Each auxiliary tubular member receives incident light from a different portion of the remote situs. The apparatus is particularly useful for conducting phototherapy in body cavities and has been demonstrated in the phototherapy treatment of superficial cancer in a bladder.

11 Claims, 3 Drawing Sheets

DEVICE FOR MEASURING INCIDENT LIGHT IN A BODY CAVITY

This application is a continuation of application Ser. No. 07/833,013 filed May 14, 1992 now abandoned.

TECHNICAL FIELD

The present invention relates to phototherapy within a body cavity. More particularly, the present invention relates to methods and apparatus for monitoring light dosage during phototherapy within a body cavity.

BACKGROUND ART

Phototherapy has been found to be an effective method of treating superficial bladder cancer and is expected to find applicability for treatment of similar and other pathological and physiological conditions in other body cavities.

In order to conduct phototherapy within a body cavity a light delivery system is required. Suitable light deliver systems only require a light source such as a laser and an optical fiber to conduct the light to a desired remote position.

To be effective, the light dosage used during phototherapy must be monitored. Too little light may not provide a desired result. On the other hand, too much light may cause adverse effects, including harm to healthy tissue.

Presently, the only method for monitoring the dosage of light delivered through an optical fiber to a remote location is to monitor the output of light at the light source itself, rather than at the remote situs. Such monitoring lacks the accuracy desired in phototherapy.

There exists a need for a method and apparatus which allows for accurate monitoring of light dosage during phototherapy within a body cavity.

DISCLOSURE OF THE INVENTION

It is accordingly one object of the present invention to provide an apparatus for phototherapy within a remote situs such as a body cavity.

Another object of the present invention is to provide a means for situs monitoring of light dosage during phototherapy within a remote situs such as a body cavity.

A further object of the present invention is to provide an apparatus for phototherapy within a remote situs such as a body cavity which includes means for situs monitoring of light dosage during phototherapy.

A still further object of the present invention is to provide a method of conducting phototherapy within a remote situs such as a body cavity.

A still further object of the present invention is to provide a method of situs monitoring of light dosage during phototherapy within a remote situs such as a body cavity.

According to these and further objects of the present invention which will become apparent as the description thereof proceeds, the present invention provides a device for detecting incident light in a remote situs which includes:

a central tubular member having first and second ends; and at least one auxiliary tubular member having first and second ends, the at least one auxiliary tubular member being substantially parallel and attached to the central tubular member, the first end of each of the at least one auxiliary tubular members being directed in a non-parallel direction with one another and with the central tubular member.

The present invention further provides for a method of measuring incident light in a remote situs which involves:

inserting a central tubular member into the remote situs together with at least one auxiliary tubular member substantially parallel and attached to the central tubular member;

delivering light to the remote situs through the central tubular member; and transmitting incident light from the remote situs through the at least one auxiliary tubular member to a light detector.

BRIEF DESCRIPTION OF DRAWINGS

The present invention will be described with reference to the attached drawings which are given by way of non-limiting examples only, in which.

BEST MODE FOR CARRYING OUT THE INVENTION

The present invention is directed to an apparatus and method for monitoring light dosage during phototherapy at a remote situs in a body cavity, e.g., in a bladder. The apparatus includes an obturator which is inserted in a cystoscope sheath. The cystoscope sheath utilized in the present invention is of a conventional design. The obturator is of a special design which includes means to deliver light to a remote situs and means to monitor light dosage delivered to the remote situs.

For delivering light to the remote situs, an optical fiber (treatment fiber) is positioned within a central tubular passage in the obturator. The optical fiber extends through the entire length of the obturator and is connected to a suitable light source such as a laser in a conventional manner.

The means to monitor light dosage at the remote situs includes a number of small auxiliary tubular passages which are provided adjacent the central tubular passage. Each of the auxiliary tubular passages is designed with a suitable inside diameter so that a single, thin optical fiber (dosimetry fiber) can be inserted therein and used to monitor light dosage.

In operation, the obturator tip is positioned in a remote situs such as a body cavity, e.g., a bladder. An optical fiber positioned in the central tubular passage delivers light from a light source to the remote situs. Optical fibers within each of the auxiliary tubular passages conduct incident light from the remote situs to a conventional light monitor. In this manner, phototherapy can be conducted while measuring light dosage at the actual, remote situs whereat the phototherapy is occurring.

Figure 1:
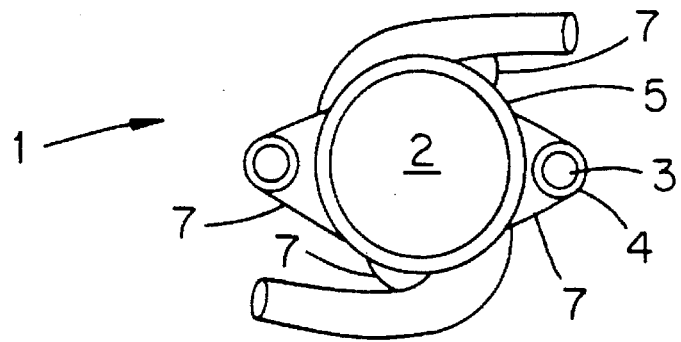
FIG. 1 is a schematic view of the tip of the obturator for a cystoscope according to one embodiment of the present invention.

FIG. 1 is a schematic view of the tip of the obturator for a cystoscope according to one embodiment of the present invention. As depicted in FIG. 1, the obturator 1 includes a central tubular member 2 through which an optical fiber (not shown) can be positioned and utilized to deliver light to a remote situs whereat the tip of the obturator is positioned.

A number of auxiliary tubular members 3 surround and are attached to the central tubular member 2 as shown. The auxiliary tubular members 3 have ends 4 which terminate in the vicinity of the end 5 of the central tubular member 2.

In use, thin, e.g., single strand optical fibers (not shown) are positioned in each of the auxiliary tubular members 3. These optical fibers are utilized to conduct incident light from the tip of the obturator to a conventional light detector or monitor located outside of the remote situs.

Figure 2:
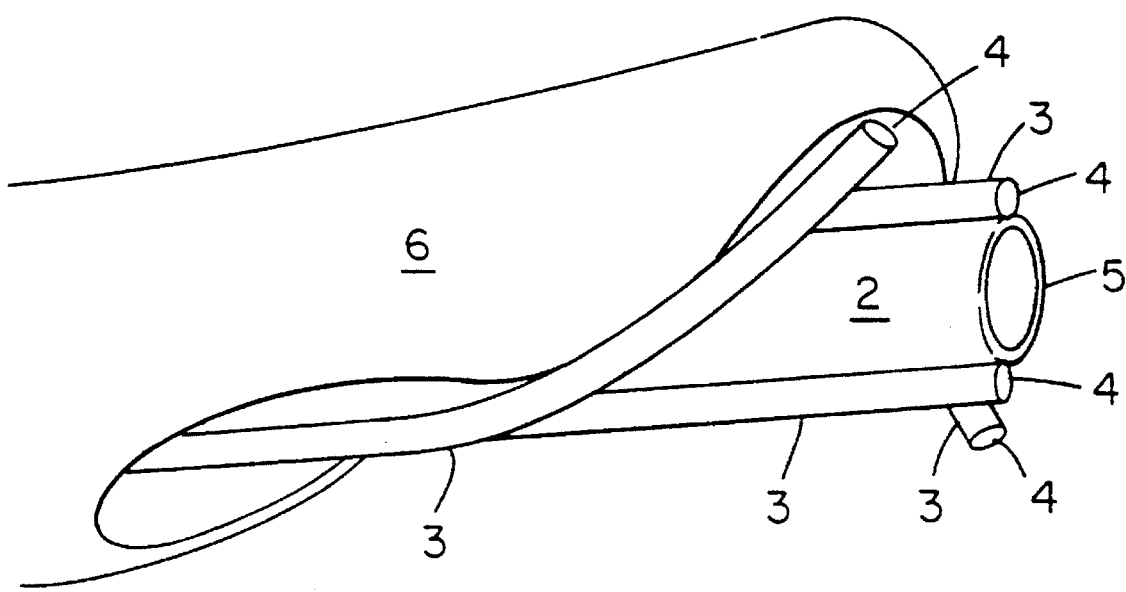
FIG. 2 is a perspective view of the tip of the obturator positioned in a sheath of a cystoscope.
Figure 5:
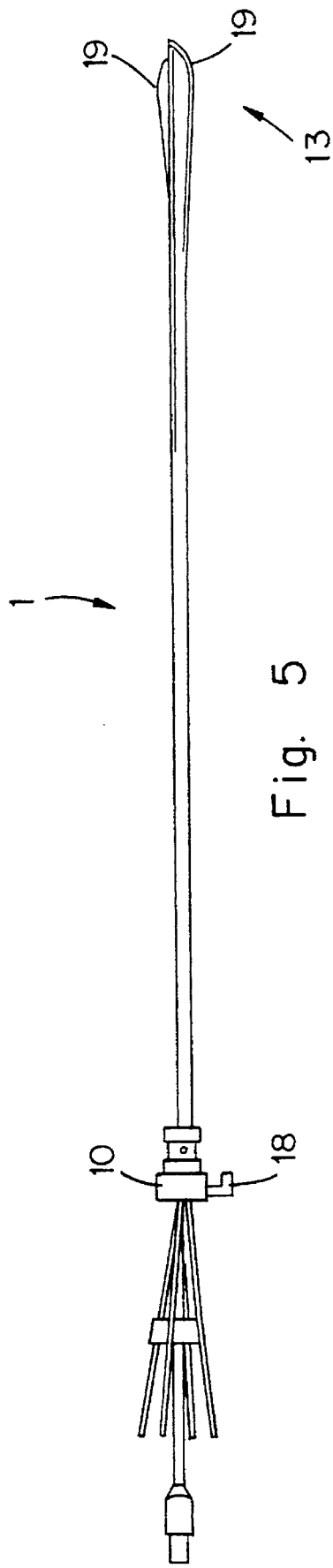
FIG. 5 is a schematic view of the obturator according to one embodiment of the present invention.

In the case of monitoring light dosage in a body cavity such as a bladder, it is preferable to monitor light from different quadrants of the cavity. Accordingly, in a preferred embodiment of the invention, each of the ends 4 of the auxiliary tubular members 3 are angled near the end 5 of the central tubular member 2 as shown in FIGS. 1, 2 and 5. This allows the optical fibers positioned in the auxiliary tubular members 3 to receive light from different areas in the body cavity. It is noted that the tips of the optical fibers positioned in the auxiliary tubular members 3 can either extend slightly beyond the ends 4 of the auxiliary tubular members 3 or otherwise be substantially flush with the ends 4 of the auxiliary tubular members 3.

FIG. 2 is a perspective view of the tip of the obturator positioned in a sheath of a cystoscope. The cystoscope sheath 6 shown in FIG. 2 is of a conventional design and is merely utilized to position the obturator 1 at a remote situs whereat phototherapy is to be conducted.

FIG. 2 (and FIG. 5) shows how the auxiliary tubular members 3 are positioned adjacent the central tubular member 2 and how the ends 4 of the auxiliary tubular members 3 are set at different angles from the end 5 of the central tubular member, and from each other.

In fabricating the obturator 1 utilizing a rigid material such a metal, e.g, stainless steel, titanium, etc., a number of auxiliary tubular members 3 are positioned parallel and adjacent the central tubular member 3 and are affixed thereto by welding, cementing, e.g, epoxying, or by other equivalent means. At the tip of the obturator, the ends 4 of the auxiliary tubular members 3 are bent or curved so as to project at different angles from the end 5 of the central tubular member 2, and from each other. In FIG. 1, a weld portion 7 is shown for illustrative purposes. The weld portion can extend substantially along the entire length of the obturator if desired. The welded portion is not shown in FIG. 2 so that the relative arrangement of the central tubular member 2 and the auxiliary tubular members 3 is visible.

It is preferable to utilize a sterilizable material, e.g., a metal from which to fabricate the obturator 1 so that the obturator 1 can be sterilized and reused. However, it is also possible to fabricate the obturator 1 from other bio-compatible materials including plastics and resinous materials. The main concern in utilizing such non-metal materials is ensuring that they are not adversely effected by heat from the light utilized in the phototherapy. It is also possible to form the auxiliary tubular members 3 so that they are integral with the wall of the central tubular member 2.

For illustrative purposes, the drawings show the use of four auxiliary tubular members 3. However, it is to be noted that any number of auxiliary tubular members 3, including a single auxiliary tubular member, could be utilized. The only factor limiting the number of auxiliary tubular members 3 is their outside diameter relative to the outside diameter of the central tubular member 2. Both the diameters of the central tubular member 2 and of the auxiliary tubular members 3 can easily be selected based upon the diameters of the optical fibers which are utilized. The apparatus of the present invention utilizes commercially available optical fibers of known diameters.

Figure 3:
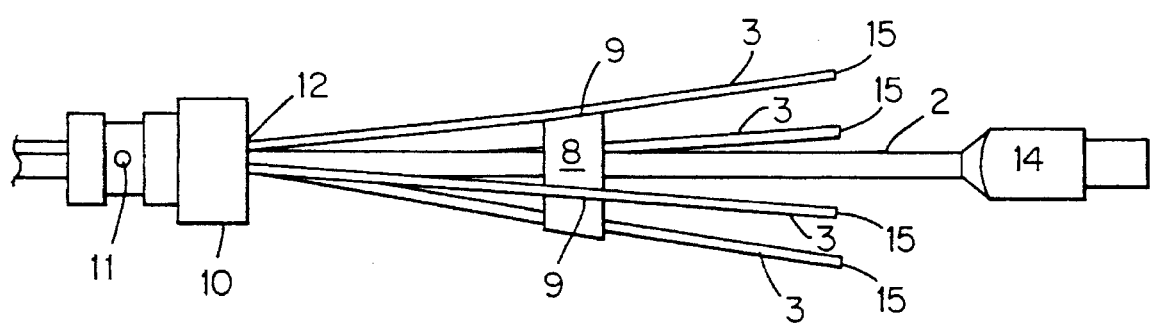
FIG. 3 is a schematic view of the end of the obturator for a cystoscope according to one embodiment of the present invention.

FIG. 3 is a schematic view of the end of the obturator for a cystoscope according to one embodiment of the present invention. At the end of the obturator 1 the ends 15 of the auxiliary tubular members 3 are ideally separated from one another. FIG. 3 shows the use of a spacer 8 in the form of a frustrum of a cone which is used to maintain separation of the ends of the auxiliary tubular members 3. The spacer 8 is made of a material, e.g., metal, which can withstand the heat of light transmitted through the central tubular member 2. The spacer 8 has a number of grooves 9 therein into which the auxiliary tubular members 3 are seated, as shown. The obturator 1 includes a connector element 10 by which the obturator 1 is connected to the cystoscope sheath 6 as discussed below. This connector element 10 is of a conventional design and includes locking pins 11 which secure the obturator 1 to the cystoscope sheath 6 as discussed below. From the end 12 of the connector element 10 to the tip 13 of the obturator 1 the auxiliary tubular members 3 are closely adjacent the central tubular member 2 as shown in FIG. 5.

The central tubular member 2 includes a conventional coupler 14 by which an optical fiber (treatment fiber) can be inserted into the central tubular member 2 and secured therein. Optical fibers (dosimeter fibers) are inserted though the ends 15 of the auxiliary tubular members 3. It is for this reason that the ends 15 of the auxiliary tubular members 3 are separated from one another. Such separation allows access to the ends 15 of each of the auxiliary tubular members 3.

Although not illustrated, the free end of an optical fiber positioned within the central tubular member 2 is connected to a conventional light source such as a laser. Likewise, the free ends of the optical fibers inserted in the auxiliary tubular members 3 are connected to one or more conventional light detectors or monitors. In a preferred embodiment, light is simultaneously monitored from each of the optical fibers inserted in the auxiliary tubular members 3. In other embodiments, light from one or more of the optical fibers inserted in the auxiliary tubular members 3 is monitored. It is also possible to alternatively scan each of the optical fibers inserted in the auxiliary tubular members 3 periodically or selectively.

Figure 4:
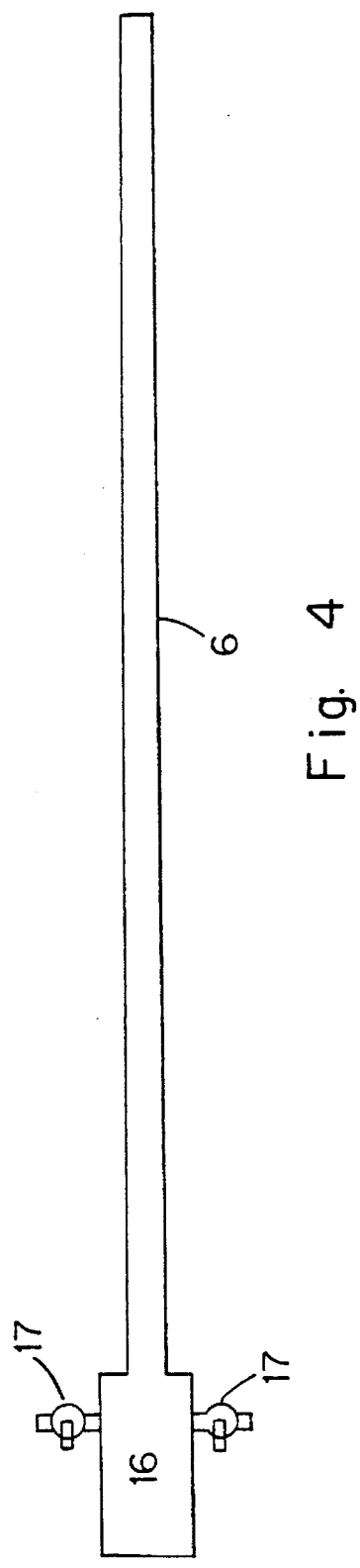
FIG. 4 is a schematic view of a cystoscope sheath.

FIG. 4 is a schematic view of a cystoscope sheath. The cystoscope sheath 6 is of conventional design and includes a connector element 16 in which the obturator 1 is inserted and to which the obturator 1 is attached. Conventional valved ports 17 are provided on the connector element 16.

FIG. 5 is a schematic view of the obturator according to one embodiment of the present invention. In FIG. 5 the connector element 10 is shown as including a lever 18 by which the obturator 1 is connected to the connector element 16 of the cystoscope sheath 6. In this regard, in a conventional manner, once connector element 10 is inserted into connector element 16, relative rotation of the connecting elements causes locking pins 11 (FIG. 3) to engage locking recesses or cams in connecting member 16. Of course, other conventional connecting means could also be utilized.

In FIG. 5 the curved ends 19 of the auxiliary tubular members 3 is slightly exaggerated so as to show how they are directed to point in different directions.

The device of the present invention has been tested in a procedure in which superficial bladder cancer was subject to phototherapy. In use, the obturator was placed in the cystoscope sheath and positioned in the bladder. The treatment fiber was inserted in the central tubular member and dosimeter fibers were inserted into each of the auxiliary tubular members. Light was supplied to the free end of the treatment fiber which delivered the phototherapy light to the wall(s) of the bladder. Light dosage within the bladder was monitored by transmitting light received by the dosimeter fibers to a light monitor.

In tests, it was determined that the use of the obturator of the present invention to monitor light dosage within a bladder was more accurate and reliable that monitoring the intensity of the light source outside of the subject's body.

The obturator of the present invention and the manner in which it was tested are applicable for use in any remote cavity in which a measurement of light intensity is desired. The device and its method of use are not limited to cavities in a subject's body.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. An obturator which comprises:
   a central hollow tubular member having first and second ends and an outer surface;
   at least one auxiliary hollow elongated cylindrical tubular member having first and second ends, and an outer surface,
   wherein each of said at least one auxiliary hollow elongated cylindrical tubular members is substantially parallel and attached directly to said outer surface of said central hollow tubular member along a contact point therebetween so that the outer surface of each of said at least one auxiliary hollow elongate tubular members is exposed except at said contact point and,
   said first end of each of said at least one auxiliary hollow elongated cylindrical tubular members is directed in a non-convergent, non-parallel direction with one another and with said central hollow tubular member and in a direction which has a forward component with respect to said first end of said central hollow tubular member and;
   means for monitoring light, said means for monitoring light being connectable to each of said at least one auxiliary hollow elongated cylindrical tubular members by optical fibers which pass through said second end of each of said at least one auxiliary hollow elongated cylindrical tubular members and conduct incident light to said means for monitoring light.

2. An obturator according to claim 1, wherein said at lease one auxiliary hollow elongated cylindrical tubular member comprises more than one auxiliary hollow elongated cylindrical tubular member.

3. An obturator according to claim 2, wherein said at least one auxiliary hollow elongated cylindrical tubular member comprises four auxiliary hollow elongated cylindrical tubular members.

4. An obturator according to claim 1, wherein each of said at least one auxiliary hollow elongated cylindrical tubular member has a diameter which is smaller than the diameter of said central hollow tubular member.

5. An obturator according to claim 1, wherein said first end of each of said at least one auxiliary hollow elongated cylindrical tubular members terminates at a position which is substantially adjacent said first end of said central hollow tubular member.

6. An obturator according to claim 1, further comprising a connector element for securing said obturator into a cystoscope sheath, said connector element being positioned near said second ends of said central hollow tubular member and said at least one auxiliary hollow elongated cylindrical tubular member.

7. An obturator according to claim 6, wherein said second end of said central hollow tubular member includes a coupler for receiving and securing an optical fiber in said central hollow tubular member.

8. An obturator according to claim 6, wherein between said connector element and said second end of said central hollow tubular member, each of said at least one auxiliary hollow elongated cylindrical tubular members extends outwardly from said central hollow tubular member at said connector element.

9. An obturator according to claim 1, wherein said central hollow tubular member and said at least one auxiliary hollow elongated cylindrical tubular member are made from a metal.

10. The obturator of claim 1 in combination with a sheath into which said obturator is positioned.

11. The obturator of claim 1 in combination with optical fibers which are positioned in each of said central tubular member and said at least one auxiliary tubular member.

* * * * *